US005135925A

United States Patent [19]

Vinas

[11] Patent Number: 5,135,925

[45] Date of Patent: Aug. 4, 1992

[54] USE OF ZINC ACEXAMATE IN THE PROPHYLAXIS OF GASTROPATHY INDUCED BY NON-STEROIDAL ANTI-INFLAMMATORY DRUGS

[75] Inventor: Antonio B. Vinas, Barcelona, Spain

[73] Assignee: Laboratorios Vinas, S.A., Barcelona, Spain

[21] Appl. No.: 644,484

[22] Filed: Jan. 18, 1991

Related U.S. Application Data

[63] Continuation of Ser. No. 505,490, Apr. 6, 1990, abandoned.

[51] Int. Cl.[5] .................. A61K 31/40; A61K 21/315; A61K 31/415; A61K 31/605

[52] U.S. Cl. .................................. 514/164; 514/404; 514/420; 514/494

[58] Field of Search ............... 514/494, 164, 404, 420

[56] References Cited

PUBLICATIONS

European Journal of Pharmacology-vol. 109, 1985, pp. 145-151 Esplugues et al. "Effects of Zinc Acexamate on Gastric Mucosal Resistance Factors".

Prostaglandins, Leukotrienes & Essential Fatty Acids, vol. 33, 1988 pp. 75'80, Longman Group Ltd., GB "Effects of zinc acexamate on gastric muscosal production of prostaglandin E2 in normal and stressed rats".

Meth. and Find. Exptl. CliniPharmaca Col. vol. 9, No. 7, 1987, pp. 423-427 G. Escolar et al., "Antiulcerogenic Activity of Zinc Acexamate in Different Experimental Models".

Postgraduate Medical Journal, vol. 64, (Suppl. 1), 1988 pp. 12-14 M. M. Cohen "Aspirin-induced gastrodnodeaal injury and its prevention by prostaglandins".

Chemical Abstracts, vol. 99, No. 10, 1983, p. 370, ref. 76901j Carpov et al. "Antiinflammatory and antirheumatic composition containing acetylsalicylic acid and aminocaproic acid".

Arch. Intern. Med., vol. 146, Jun. 1986, pp. 1075-1076, S. H. Roth "Nonsteroidal Anti-inflammatory Drug Gastropathy".

Chem. Abst. 105-145966R (1986).

Chem. Abst. 106-188991H (1987).

*Primary Examiner*—S. J. Friedman

*Attorney, Agent, or Firm*—Dressler, Goldsmith, Shore, Sutker & Milnamow, Ltd.

[57] ABSTRACT

Zinc acexamate acts by increasing the synthesis of mucus, reinforces the mucous barrier, improves the microcirculation and increases the synthesis of prostaglandins in the gastric mucous membrane, whereby it is effective in the treatment of said gastropathy, contrary to the results obtained with antiacids or antisecretory agents.

15 Claims, No Drawings

USE OF ZINC ACEXAMATE IN THE PROPHYLAXIS OF GASTROPATHY INDUCED BY NON-STEROIDAL ANTI-INFLAMMATORY DRUGS

This application is a continuation, of application Ser. No. 07/505,490, filed Apr. 6, 1990, now abandoned.

The present invention relates to a novel utilization of zinc acexamate for the prophylaxis of gastropathy induced by non-steroidal anti-inflammatory drugs (hereinafter referred to as NSAIDs).

Previous therapeutical uses of zinc acexamate are already known. This agent has shown itself to be active in gastric and peptic ulcer obtaining a high percentage of healing and a low rate of relapse in maintenance treatments. However the effect of antiulcer drugs in drug-induced gastropathy is unclear at the moment.

For instance, $H_2$ antihistaminic drugs, the standard agents for the treatment of gastric and duodenal ulcer have not shown themselves to be useful in drug gastropathy either in experimental (Kauffman et al., 1979, Proc. Soc. Exp. Biol. Med., 161: 512-4) or clinical setting (Roth et al., 1987, Arch. Int. Med., 147: 1798-801). For this reason, etiopathogenic differences between peptic ulcer and gastric toxicity of NSAIDs have been suggested (Roth et al., 1987, Arch. Int. Med., 147: 1798-801).

Gastric toxicity is one of the most frequent side effects of NSAIDs.

This toxicity shows effects ranging from asymptomatic gastric erosions to hematemeses which may place the patient's life in serious danger. In patients having to take such preparations for long periods of time as in rheumatic patients, ferropenic anaemias are not infrequently observed as a result of the chronic loss of blood through the digestive tract. Likewise, the appearance of digestive disorders may not be an absolute indication of suppression of the treatment in patients suffering from an attack of acute arthritis.

Although with certain differences, it is agreed that all the NSAIDs have undesirable effects on the gastric apparatus. Two essential mechanisms have been pointed out in the production of this toxicity. The first is allegedly the result of a local effect on the mucous membrane caused by direct irritation by the drug, since the majority of the NSAIDs are weak acids which would damage cells until destroying them: this would be accompanied by an alteration of the gastric mucous barrier with an increase in the retrodiffusion of hydrogen ions and damage to the submucous structures. But this local mechanism would not completely explain the harmful action of the NSAIDs on the gastric system, since the lesions also appear when administered parenterally. It should therefore be contemplated that these drugs may also affect the synthesis of the gastric mucous membrane prostaglandin, particularly those which protect it against the acid and aggressive exogenous substances. The predominant prostaglandins in the mucous membrane are $PGI_2$ and $PGE_2$ Among their physiological functions are those of stimulation the mucus secretion, reinforcement of the mucous barrier and improvement of the microcirculation. They can also reduce the acid secretion. Therefore, if the synthesis thereof is inhibited, the stomach becomes more sensitive to the action of any irritating factor.

The research directed towards reducing the gastric effects of the NSAIDs while maintaining their anti-inflammatory potency has not been very successful. It would appear that both actions go hand-in-hand and are, at present, inseparable. Neither antiacids nor antisecretory drugs have shown themselves to be effective to prevent the harmful gastric effects of the NSAIDs. This was to be expected, if their special features are taken into account. Among the essential differences between a gastroduodenal ulcerous disorder treated correctly with anti-secretory drugs and the gastric pathology of the NSAIDs, there are the initial clinical picture (with little or no symptomatology with the NSAIDs), the demography (more women than men), the location of the NSAID-induced lesions (more in fundus, antrum and pre-pyloric region) and the physiopathological production mechanism (inhibition of prostaglandin synthesis). This has led certain authors such as Roth (1986, Arch. Intern. Med., 146: 1075-6) to talk of NSAID-induced gastropathy, to define the clinical picture offered by these patients.

The ageing of the Western population involves an increase in NSAIDs consumption, due to the presence of rheumatic diseases advising the use thereof. Therefore, the number of exposed patients means that the risk of gastric toxicity is high. It has been reported that in certain countries, 50% of upper digestive hemorrhages are due to ingestion of salicylates, while the remaining NSAIDs represent a further 20%. No drug has shown itself to be therapeutically useful to prevent the appearance of this pathology, particularly important in patients who, like the rheumatic ones, are obliged to take NSAIDs, since there is no alternative treatment for their disease.

Zinc acexamate is a modern drug which acts by increasing the synthesis of mucus, reinforcing the mucous barrier, improving the microcirculation, inhibiting degranulation of the mastocytes and increasing the synthesis of prostaglandins in the gastric mucous membrane (Esplugues et al., 1985, Eur. J. Pharmacol., 109: 145-51; Esplugues et al., 1987, Arch. Int. Pharmacodyn. Ther., 290: 128-37; Navarro et al., 1988, Prostaglandins, Leukotrienes and Essential Fatty Acids, 33: 75-80).

One object of the present invention is therefore to provide a method of treating NSAID-induced gastropathy by producing a composition in which zinc acexamate is the main active principle.

Another object of the present invention is to provide a pharmaceutical composition containing zinc acexamate.

This composition possesses a protective activity against toxicity by NSAIDs, and is useful in the prevention of gastropathy caused by therapy with NSAIDs.

A further object of the invention is to provide a medicament useful for the prophylaxis of gastropathy caused by the administration of NSAIDs.

The invention also provides for the use of zinc acexamate, for the manufacture of a medicament, for the prevention or for the prophylactic treatment of gastropathy caused by the administration of NSAIDs.

The preventive effect of zinc acexamate (ZAC) on NSAID-induced gastric lesions is studied.

The use of non-steroidal anti-inflammatory drugs (NSAIDs) for treating different types of pain pathology is widespread (Hart, F. D. et al., 1984). This type of drugs forms a heterogenous group of compounds having different chemical groups combining with their therapeutical properties the drawbacks of their side effects. Among the anti-inflammatory drugs known for their harmful gastric activity is the group of the socalled "aspirin-like" drugs including aspirin, indomethacin, phenylbutazone and ibuprofen (Pfeiffer C. J., 1982, Drugs and Peptic Ulcer, Vol. II, C.R.C. Press, Inc.).

The effects of these substances on the gastric mucous membrane have been widely studied, and are significantly similar in man and in the rat. From a practical point of view, the most interesting aspect of these studies is to be found in using the results obtained to improve the gastric tolerance to these NSAIDs, while maintaining their anti-inflammatory activity.

In view of the more or less serious gastric intolerance to the different anti-inflammatory drugs, the possibility of inhibiting this side effect by way of the protective action of zinc acexamate (ZAC) has been considered. Therefore, the protective effect of ZAC against gastric lesions induced by the most characteristic NSAIDs has been studied. The animal of election was the rat (Sprague Dawley). which was sacrificed after treatment with ZAC and NSAID. The stomach was extirpated, and macro and microscopic evaluations were made. The macroscopic evaluation was made following the method of Adami (1964, Arch. Int. Pharmacodyn., 147: 113-45) with slight modifications, consisting of evaluating the gravity and extension of the lesions, using a points system evaluating the lesions according to the number and/or size thereof.

0 - no lesion
1 - irritation or presence of a hemorrhagic area
2 - from 1 to 5 small ulcers
3 - many small ulcers (more than 5) or 1 large one
4 - many large ulcers
5 - perforated ulcer The overall value of the lesions is obtained by adding up the score of the lesions determined.

An additional anti-ulcer activity index was calculated for phenylbutazone, obtained by expressing the lesion indexes as an inhibition percentage relative to the control group. The dose-response curve was determined from the percentages and the theoretical $ED_{50}$ was determined from the curve.

Half of the stomachs of each animal group was taken for hystological processing, the microscopic lesions being valued according to a scale of 0 to 5, 0 being a lesion-free mucous membrane and 5 representing multiple erosions with hemorrhagic subfusions.

The different anti-inflammatory dosage levels and the ZAC levels studied for the different groups of anti-inflammatory drugs are given below. The administration parameters were as follows:

Aspirin: two doses of 200 mg/kg p.o. were administered spaced apart by 12 hours.

Ibuprofen: a single 200 mg/kg dose was administered

In both cases, ZAC was tested at dosages of: 50, 100 and 150 mg/kg and a control group received water.

A total dose of 80 mg/kg of phenylbutazone was administered, half at the start of the experiment and the other half after 2 hours. The ZAC doses used were 75, 150 and 300 mg/kg. The animals were sacrificed 4 hours after the last ZAC administration.

The total dose of indomethacin used was 20 mg/kg, in two divided doses of 10 mg/kg, spaced apart by 12 hours. 200 mg/kg of ZAC was administered. The animals were sacrificed 2 hours after the administration of the last dose.

RESULTS

Example 1

Aspirin-induced lesions

| | a) Macroscopic index: | | | |
|---|---|---|---|---|
| | Control | ZAC 50 | ZAC 100 | ZAC 150 |
| n | 10 | 10 | 10 | 10 |
| x ± SD | 3.4 ± 0.2 | 2.3 ± 0.3 ** | 2.1 ± 0.3 ** | 1.9 ± 0.3 ** |
| | **b) Microscopic index:** | | | |
| | Control | ZAC 50 | ZAC 100 | ZAC 150 |
| n | 10 | 10 | 10 | 10 |
| x ± SD | 3.0 ± 0.3 | 1.8 ± 0.2 ** | 2.0 ± 0.2 ** | 2.3 ± 0.2 ** |

Example 2

Ibuprofen-induced lesions

| | a) Macroscopic index: | | | |
|---|---|---|---|---|
| | Control | ZAC 50 | ZAC 100 | ZAC 150 |
| n | 10 | 10 | 10 | 10 |
| x ± SD | 2.4 ± 0.3 | 1.6 ± 0.4 ** | 1.7 ± 0.3 ** | 1.5 ± 0.2 ** |
| | **b) Microscopic index:** | | | |
| | Control | ZAC 50 | ZAC 100 | ZAC 150 |
| n | 10 | 10 | 10 | 10 |
| x ± SD | 2.8 ± 0.4 | 2.2 ± 0.2 * | 2.4 ± 0.2 NS | 2.0 ± 0.03 ** |

Example 3

Phenylbutazone-induced lesions

| | a) Macroscopic index | | | |
|---|---|---|---|---|
| | Control | ZAC 75 | ZAC 150 | ZAC 300 |
| n | 10 | 10 | 10 | 10 |
| x ± SD | 2.8 ± 0.4 | 1.3 ± 0.5 ** | 0.4 ± 0.3 ** | 2.0 ± 0.2 ** |

Example 4

Indomethacin-induced lesions

| | a) Macroscopic index: | |
|---|---|---|
| | Control | ZAC 200 |
| n | 10 | 10 |
| x ± SD | 4.3 ± 0.4 | 1.8 ± 0.3 ** |
| | **b) Microscopic index:** | |
| | Control | ZAC 200 |
| n | 5 | 5 |
| x ± SD | 4.0 ± 0.7 | 2.1 ± 0.2 ** |

*$p < 0.05$
**$p < 0.01$

Statistical analysis: Student's test was used for comparison

Results are expressed as ± standard deviation (SD).

These results show the protective effect of zinc acexamate on NSAID-induced gastric lesions studied, both macroscopically and microscopically.

The results found in the prevention of NSAID-induced gastropathy by the administration of zinc acexamate are surprising, since it is not possible to associate these effects directly with the anti-ulcer curative effects reported for this product and for other anti-secretory or antiacid products.

These results provide a new preventive treatment for any NSAID-induced gastropathy.

The applications are very extensive and varied, if the wide variety of indications under which the NSAIDs are used, such as pains of any ethiology (headache, otalgia, toothache, dysmenorrhea, traumatism) and rheumatic processes (rheumatoid arthritis, osteoarthritis, spondylitis ankylopoietica) are considered.

In all cases where the NSAIDs are required, particularly in cases requiring repeated or chronic administration, zinc acexamate, as disclosed herein, is very useful, when administered prior to or jointly with the NSAIDs, in a single dose or in divided doses, to avoid the toxic effects the latter may produce.

For the new therapeutic application, according to the invention, the formulation should contain zinc acexamate as active principle, alone or associated with an anti-inflammatory drug.

To prepare a pharmaceutical composition according to the invention, a formulation for convenient oral administration will be prepared.

Thus, if a solid carrier is used, the preparation may be a tablet, placed in a hard gelatine capsule in powder or granular form, or in form of troche, or capsule.

If a liquid carrier is employed, the preparation may be in form of a syrup, emulsion, soft gelatin capsule, or an aqueous or non-aqueous liquid suspension. The pharmaceutical composition are prepared by conventional techniques appropriated to the desired preparation.

Depending upon the dosage forms employed the products of this invention may also contain other adjuvants that may be useful in formulating the particular dosage form or in its administration. Thus, for example, when administered as a tablet, the products of this invention may also contain: lubricants, excipients, binding agents, disintegrating agents, flavoring agents, etc.

When administered in capsule form, these may contain agglutinants, lubricants, humectants, disintegrating agents, etc.

Each dose of the composition should contain between 20 and 500 mg of zinc acexamate, either alone or associated in the same formulation with an anti-inflammatory agent at the chosen effective anti-inflammatory dose. Where it is presented in association with a NSAID, the usual dose of the latter varies between 20 mg and about 300 mg.

The particular dosage depends on the effect desired and on the administration route. For example the dosage may be between 80 and 2,000 mg of zinc acexamate per day, alone or associated with the chosen anti-inflammatory drug.

Some possible pharmaceutical composition may be the following:

| Preparation No. 1 | |
|---|---|
| Zinc acexamate | 300 mg |
| Maize starch (agglutinant) | 70 mg |
| Lactose | 50 mg |
| Polyethylene Glycol 4000 (humectant) | 21 mg |
| Talcum powder (lubricant) | 15 mg |
| Polyvinylpyrrolidone or Plasdone (agglutinant) | 10 mg |
| Starch Glycollated Sodium or Explotab (disintegrating agent) | 8 mg |

-continued

| | |
|---|---|
| Tween 80 (humectant) | 0.5 mg |
| For one capsule of 484.5 mg | |
| Preparation No. 2 | |
| Zinc acexamate | 300 mg |
| Dehydrated calcium sulphate | 80 mg |
| Maize starch (agglutinant) | 50.9 mg |
| Talcum powder (lubricant) | 20 mg |
| Starch Glycollated Sodium or Explotab (disintegrating agent) | 10 mg |
| Polyvinylpyrrolidone or Plasdone (agglutinant) | 5 mg |
| Tween 80 (humectant) | 0.1 mg |
| For one tablet of 466 mg | |
| Preparation No. 3 | |
| Zinc acexamate | 300 mg |
| Ibuprofen | 200 mg |
| Saccharose | 500 mg |
| Sodium bicarbonate | 500 mg |
| Tartaric acid | 445 mg |
| Orange essence in powder (flavouring agent) | 30 mg |
| Sodium saccharine (sweetening agent) | 25 mg |
| For a sachet of 2,000 mg of effervescent powder | |
| Preparation No. 4 | % w/v |
| Zinc acexamate | 5.000 |
| Potassium Hydrogen Phosphate | 2.000 |
| Sodium saccharine (sweetening agent) | 0.416 |
| Orange essence (flavouring agent) | 0.700 |
| Sodium Methylparaben (preservative) | 0.070 |
| Propylparaben (preservative) | 0.030 |
| Syrup q.s. ad | 100 ml solution |

I claim:

1. A pharmaceutical composition for the treatment of pain in a human patient comprising a therapeutically effective amount for pain relief of a non-steroidal anti-inflammatory drug and a therapeutically effective amount for relief of gastropathy caused by the administration of said non-steroidal anti-inflammatory drug of zinc acexamate.

2. The composition of claim 1 wherein said non-steroidal anti-inflammatory drug is aspirin.

3. The composition of claim 1 wherein said non-steroidal anti-inflammatory drug is ibuprofen.

4. The composition of claim 1 wherein said non-steroidal anti-inflammatory drug is phenylbutazone.

5. The composition of claim 1 wherein said non-steroidal anti-inflammatory drug is indomethacin.

6. The composition of claim 1 in a liquid carrier.

7. The composition of claim 1 in a solid carrier.

8. A process for the treatment of pain in a human patient which comprises administering to said patient a therapeutically effective amount for the relief of pain of a non-steroid anti-inflammatory drug together with a therapeutically effective amount for the relief of gastropathy caused by the administration of said non-steroid anti-inflammatory drug of zinc acexamate.

9. The process of claim 8 wherein said non-steroidal anti-inflammatory drug and said zinc acexamate are administered jointly in a single dose.

10. The process of claim 8 wherein said zinc acexamate is administered prior to the administration of said non-steroidal anti-inflammatory drug.

11. The process of claim 8 wherein said non-steroidal anti-inflammatory drug and said zinc acexamate are administered orally.

12. The composition of claim 8 wherein said non-steroidal anti-inflammatory drug is aspirin.

13. The composition of claim 8 wherein said non-steroidal anti-inflammatory drug is ibuprofen.

14. The composition of claim 8 wherein said non-steroidal anti-inflammatory drug is phenylbutazone.

15. The composition of claim 8 wherein said non-steroidal anti-inflammatory drug is indomethacin.

* * * * *